United States Patent
P V R

(10) Patent No.: US 10,932,791 B2
(45) Date of Patent: Mar. 2, 2021

(54) REPOSABLE MULTI-FIRE SURGICAL CLIP APPLIER

(71) Applicant: Covidien LP, Mansfield, MA (US)

(72) Inventor: Mohan P V R, Andhra Pradesh (IN)

(73) Assignee: COVIDIEN LP, Mansfield, MA (US)

( * ) Notice: Subject to any disclaimer, the term of this patent is extended or adjusted under 35 U.S.C. 154(b) by 204 days.

(21) Appl. No.: 16/126,257

(22) Filed: Sep. 10, 2018

(65) Prior Publication Data

US 2019/0133593 A1    May 9, 2019

Related U.S. Application Data

(60) Provisional application No. 62/581,058, filed on Nov. 3, 2017.

(51) Int. Cl.
  *A61B 17/128*   (2006.01)
  *A61B 17/00*    (2006.01)
  *A61B 17/29*    (2006.01)

(52) U.S. Cl.
  CPC ........ *A61B 17/128* (2013.01); *A61B 17/1285* (2013.01); *A61B 2017/0023* (2013.01); *A61B 2017/0046* (2013.01); *A61B 2017/00367* (2013.01); *A61B 2017/00407* (2013.01);
  (Continued)

(58) Field of Classification Search
  CPC ..... A61B 17/10; A61B 17/105; A61B 17/128; A61B 17/1285; A61B 17/068; A61B 17/0682; A61B 17/07207
  See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

Extended European Search Report corresponding to Patent Application EP 18154617.7 dated Jun. 25, 2018.

(Continued)

*Primary Examiner* — Ashley L Fishback
*Assistant Examiner* — Uyen N Vo

(57) ABSTRACT

A reposable surgical clip applier includes a handle assembly, a shaft assembly engagable with the handle assembly, and a clip cartridge assembly including surgical clips engagable within the shaft assembly. The handle assembly includes a trigger, a drive bar coupled to the trigger and including a rack, a pawl configured to engage the rack upon movement of the drive bar, and a release mechanism operable to move the pawl to disengage the pawl from the rack. The shaft assembly includes an outer tube having a pair of jaws supported at a distal end portion thereof and a drive assembly slidably disposed therein. When the shaft assembly is engaged with the handle assembly and the clip cartridge assembly is engaged within the shaft assembly, actuation of the trigger loads a clip into the jaws and cams the jaws towards one another to form the clip about tissue.

18 Claims, 11 Drawing Sheets

(52) U.S. Cl.
CPC .............. *A61B 2017/00473* (2013.01); *A61B 2017/00477* (2013.01); *A61B 2017/2922* (2013.01)

(56) References Cited

U.S. PATENT DOCUMENTS

| | | |
|---|---|---|
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Faille et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |

(56) References Cited

U.S. PATENT DOCUMENTS

| | | |
|---|---|---|
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A * | 5/2000 | Aranyi et al. ............ 606/143 |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |

(56) References Cited

U.S. PATENT DOCUMENTS

| | | |
|---|---|---|
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B2 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |

(56) References Cited

U.S. PATENT DOCUMENTS

| | | |
|---|---|---|
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |

(56) References Cited

U.S. PATENT DOCUMENTS

| | | |
|---|---|---|
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Kranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0165435 A1* | 7/2005 | Johnston et al. ............ 606/167 |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | A. Morris |
| 2007/0093790 A1* | 4/2007 | Downey et al. ............ 606/1 |
| 2007/0093856 A1* | 4/2007 | Whitfield et al. ............ 606/142 |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |

(56) References Cited

U.S. PATENT DOCUMENTS

| | | |
|---|---|---|
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0248577 A1* | 9/2013 | Leimbach ............ A61B 17/072 227/175.2 |
| 2013/0253540 A1 | 9/2013 | Castro et al. |
| 2013/0334284 A1* | 12/2013 | Swayze ............ A61B 17/32053 227/180.1 |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0265282 A1 | 9/2015 | Miles et al. |
| 2015/0359536 A1* | 12/2015 | Cropper ............... A61B 17/105 227/177.1 |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0245921 A1 | 8/2017 | Joseph et al. |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202007003398 U1 | 6/2007 |
| WO | 0042922 A1 | 7/2000 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

(56) References Cited

OTHER PUBLICATIONS

International Search Report dated Mar. 11, 2019, issued in PCT/US2018/057221.

* cited by examiner

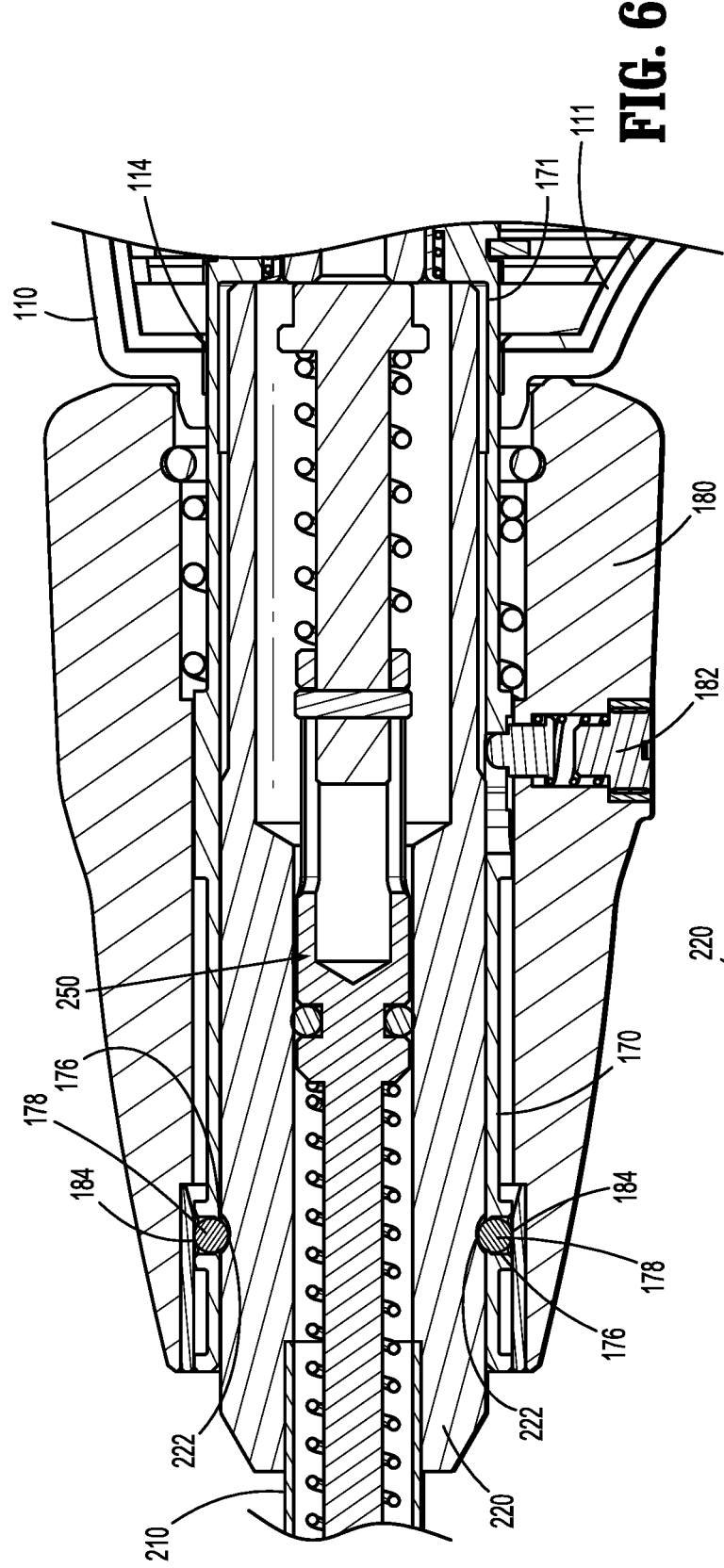
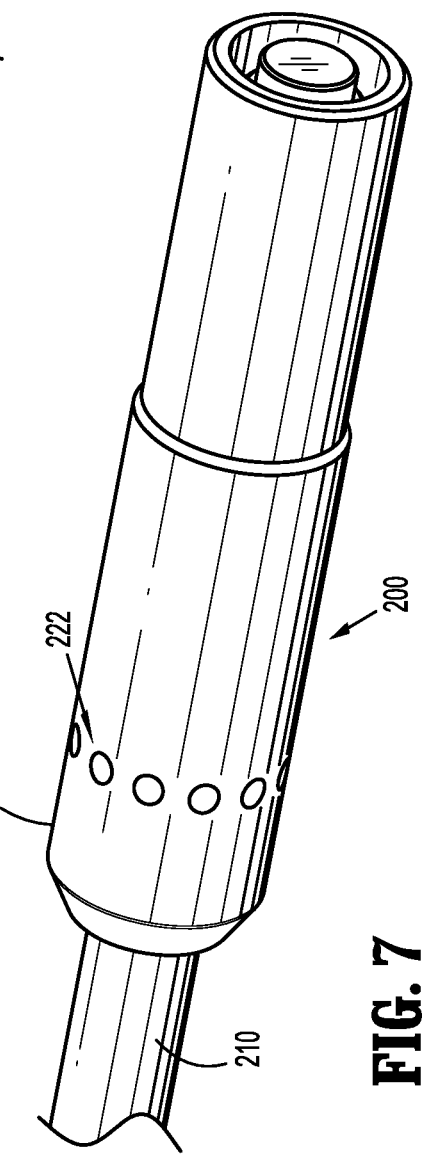
FIG. 6
FIG. 7

REPOSABLE MULTI-FIRE SURGICAL CLIP APPLIER

CROSS-REFERENCE TO RELATED APPLICATION

This application claims the benefit of and priority to U.S. Provisional Patent Application No. 62/581,058 filed Nov. 3, 2017, the entire disclosure of which is incorporated by reference herein.

BACKGROUND

Technical Field

The present disclosure relates to surgical clip appliers and, more particularly, to a reposable multi-fire surgical clip applier including a handle assembly, a shaft assembly, and a clip cartridge assembly that are configured for selective disassembly to facilitate disposable of any disposable component(s) and reprocessing of any reusable component(s) for further use.

Description of Related Art

Various staplers and clip appliers are known in the art and used for a number of distinct and useful surgical procedures. Clip appliers that are able to apply multiple clips during a single entry into a body cavity, for example, are described in commonly-assigned U.S. Pat. Nos. 5,084,057 and 5,100,420 to Green et al., the entire contents of which are incorporated herein by reference. Another multiple clip applier is disclosed in commonly-assigned U.S. Pat. No. 5,607,436 by Pratt et al., the entire contents of which is also hereby incorporated herein by reference. U.S. Pat. No. 5,695,502 to Pier et al., the entire contents of which is hereby incorporated herein by reference, discloses a resterilizable surgical clip applier that is configured to receive and cooperate with an interchangeable clip magazine so as to advance and form multiple clips during a single entry into a body cavity.

SUMMARY

The present disclosure relates to a reposable multi-fire surgical clip applier including a handle assembly, a shaft assembly, and a clip cartridge assembly that are configured for selective disassembly to facilitate disposable of any disposable component(s) and reprocessing of any reusable component(s) for further use.

A reposable surgical clip applier provided in accordance with aspects of the present disclosure includes a handle assembly, a shaft assembly releasably engagable with the handle assembly, and a clip cartridge assembly releasably engagable within the shaft assembly.

The handle assembly includes a housing, a trigger movable relative to the housing, a drive bar including a ratchet rack disposed within the housing and operably coupled to the trigger such that actuation of the trigger moves the drive bar distally through the housing, a ratchet pawl disposed within the housing, and a release mechanism. In an operable position of the ratchet pawl, the ratchet pawl is configured to incrementally engage the ratchet rack upon distal movement of the drive bar. The release mechanism includes a release button and a shaft extending from the release button. The release button is selectively actuatable to urge the shaft into the ratchet pawl, thereby moving the ratchet pawl from the operable position to a disengaged position, wherein the ratchet pawl is disengaged from the ratchet rack.

The shaft assembly includes an outer tube, a pair of jaws supported at a distal end portion of the outer tube, and a drive assembly slidably disposed within the outer tube.

The clip cartridge assembly is releasably engagable within the shaft assembly and includes a stack of surgical clips operably supported therein.

When the shaft assembly is releasably engaged with the handle assembly and the clip cartridge assembly is releasably engaged within the shaft assembly, actuation of the trigger moves the drive assembly distally to load a distal-most clip of the stack of surgical clips into the pair of jaws, and to cam the pair of jaws towards one another to form the distal-most clip about tissue.

In aspects of the present disclosure, the reposable surgical clip applier further includes a pawl biasing member configured to bias the ratchet pawl towards the operable position.

In aspects of the present disclosure, the ratchet pawl is pivotably coupled to the housing about a pawl pin, and the shaft of the release mechanism is configured to urge the ratchet pawl to pivot about the pawl pin from the operable position to the disengaged position.

In aspects of the present disclosure, a biasing member is configured to bias the drive bar proximally relative to the housing such that, upon disengagement of the ratchet pawl from the ratchet rack, the drive bar is returned proximally under the bias of the biasing member.

In aspects of the present disclosure, the release button is movable between an un-actuated position, wherein the release button extends proximally from the housing, and an actuated position, wherein the release button is depressed at least partially into the housing. In such aspects, a biasing member may be provided and configured to bias the release button towards the un-actuated position.

In aspects of the present disclosure, the outer tube of the shaft assembly defines an elongated cut-out configured to removably receive the clip cartridge assembly to releasably engage the clip cartridge assembly within the shaft assembly. In such aspects, the clip cartridge assembly may include a locking slider movable between an unlocked position and a locked position to releasably lock the clip cartridge assembly within the outer tube.

In aspects of the present disclosure, the handle assembly further includes a receiver tube extending distally from the housing. The receiver tube defines an interior and includes a plurality of ball bearings arranged circumferentially thereabout and extending partially into the interior. In such aspects, the shaft assembly includes a proximal collar defining a plurality of dimples arranged circumferentially thereabout and configured to receive the ball bearings upon insertion of the proximal collar into the receiver tube to engage the shaft assembly with the handle assembly. Further, a rotation knob may be disposed about and engaged with the receiver tube and configured such that, with the shaft assembly engaged with the handle assembly, rotation of the rotation knob relative to the housing similarly rotates the shaft assembly relative to the housing.

Another reposable surgical clip applier provided in accordance with aspects of the present disclosure includes a handle assembly, a shaft assembly releasably engagable with the handle assembly, and a clip cartridge assembly releasably engagable within the shaft assembly.

The handle assembly includes a trigger and a drive bar operably coupled to the trigger such that actuation of the trigger moves the drive bar distally.

The shaft assembly includes an outer tube, a pair of jaws supported at a distal end portion of the outer tube, and a drive assembly slidably disposed within the outer tube. The drive assembly includes a jaws-engaging portion and a first wedge.

The clip cartridge assembly including a clip carrier, a stack of surgical clips supported on the clip carrier, and a clip pusher slidable relative to the clip carrier. The clip pusher includes a second wedge pivotably coupled thereto towards a proximal end portion thereof.

When the shaft assembly is releasably engaged with the handle assembly and the clip cartridge assembly is releasably engaged within the shaft assembly, the first wedge is operably positioned relative to the second wedge and the drive bar is operably positioned relative to the drive assembly such that actuation of the trigger moves the drive assembly distally to move the clip pusher distally to load a distal-most clip of the stack of surgical clips into the pair of jaws, and to move the jaws-engaging portion distally to cam the pair of jaws towards one another to form the distal-most clip about tissue.

In aspects of the present disclosure, the clip pusher includes a wedge base disposed at a proximal end portion thereof. The wedge base includes pair of spaced-apart walls. A pivot pin extends between the spaced-apart walls to pivotably couple the second wedge to the wedge base towards a proximal end portion thereof. Further, a torsion spring may be disposed about the pivot pin and configured to bias the second wedge to extend from the wedge base.

In aspects of the present disclosure, the drive assembly of the shaft assembly includes a proximal drive assembly and a distal drive plate extending distally from the proximal drive assembly. In such aspects, the first wedge is disposed on the distal drive plate of the drive assembly. Additionally or alternatively, the distal drive plate defines the jaws-engaging portion at a distal end portion thereof.

In aspects of the present disclosure, the proximal drive assembly of the shaft assembly includes a plunger, a drive shaft coupled to and extending distally from the plunger, a first biasing member configured to bias the drive shaft proximally relative to the outer tube, and a second biasing member configured to bias the plunger proximally relative to the drive shaft. In such aspects, the first biasing member may define a spring constant that is less than a spring constant of the second biasing member such that, upon initial distal urging of the plunger, the first spring compresses to enable the plunger and the drive shaft to move together distally through the outer tube, and such that, upon further distal urging of the plunger, the second spring compresses such that the plunger moves distally through the outer tube independently of the drive shaft.

In aspects of the present disclosure, the outer tube of the shaft assembly defines an elongated cut-out. In such aspects, the clip cartridge assembly is removably insertable into the elongated cut-out to releasably engage the clip cartridge assembly within the shaft assembly. The clip cartridge assembly may further include a locking slider movable between an unlocked position and a locked position to releasably lock the clip cartridge assembly within the outer tube.

In aspects of the present disclosure, the drive bar of the handle assembly includes a ratchet rack disposed thereon and the handle assembly further includes a ratchet pawl configured to incrementally engage the ratchet rack upon distal advancement of the drive bar.

BRIEF DESCRIPTION OF THE DRAWINGS

Aspects and features of a reposable multi-fire surgical clip applier are provided in accordance with the present disclosure with reference to the drawings wherein:

FIG. 6 is an enlarged, side, longitudinal, cross-sectional view of the area of detail indicated as "6" in FIG. 5;

FIG. 7 is a side, perspective view of a proximal portion of the shaft assembly of the clip applier of FIG. 1;

DETAILED DESCRIPTION

Figure 1:
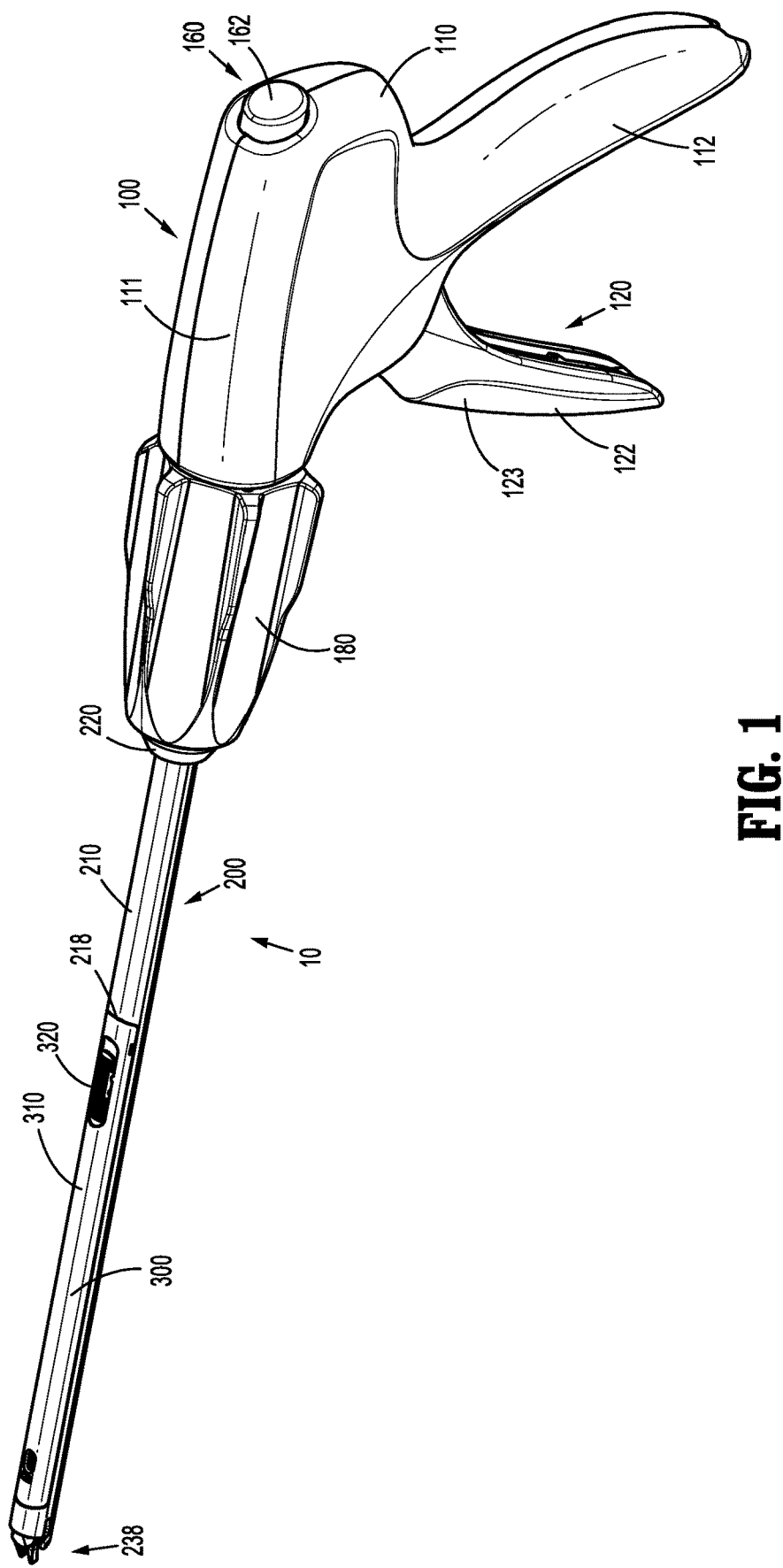
FIG. 1 is a side, perspective view of a reposable multi-fire surgical clip applier provided in accordance with the present disclosure, disposed in an assembled condition.

A reposable multi-fire surgical clip applier in accordance with the present disclosure is described in detail below with reference to the drawing figures wherein like reference numerals identify similar or identical structural elements. As shown in the drawings and described throughout the following description, as is traditional when referring to relative positioning on a surgical instrument, the term "proximal" refers to the end portion of the apparatus or component thereof which is closer to the user and the term "distal" refers to the end portion of the apparatus or component thereof which is further away from the user.

Figure 2:
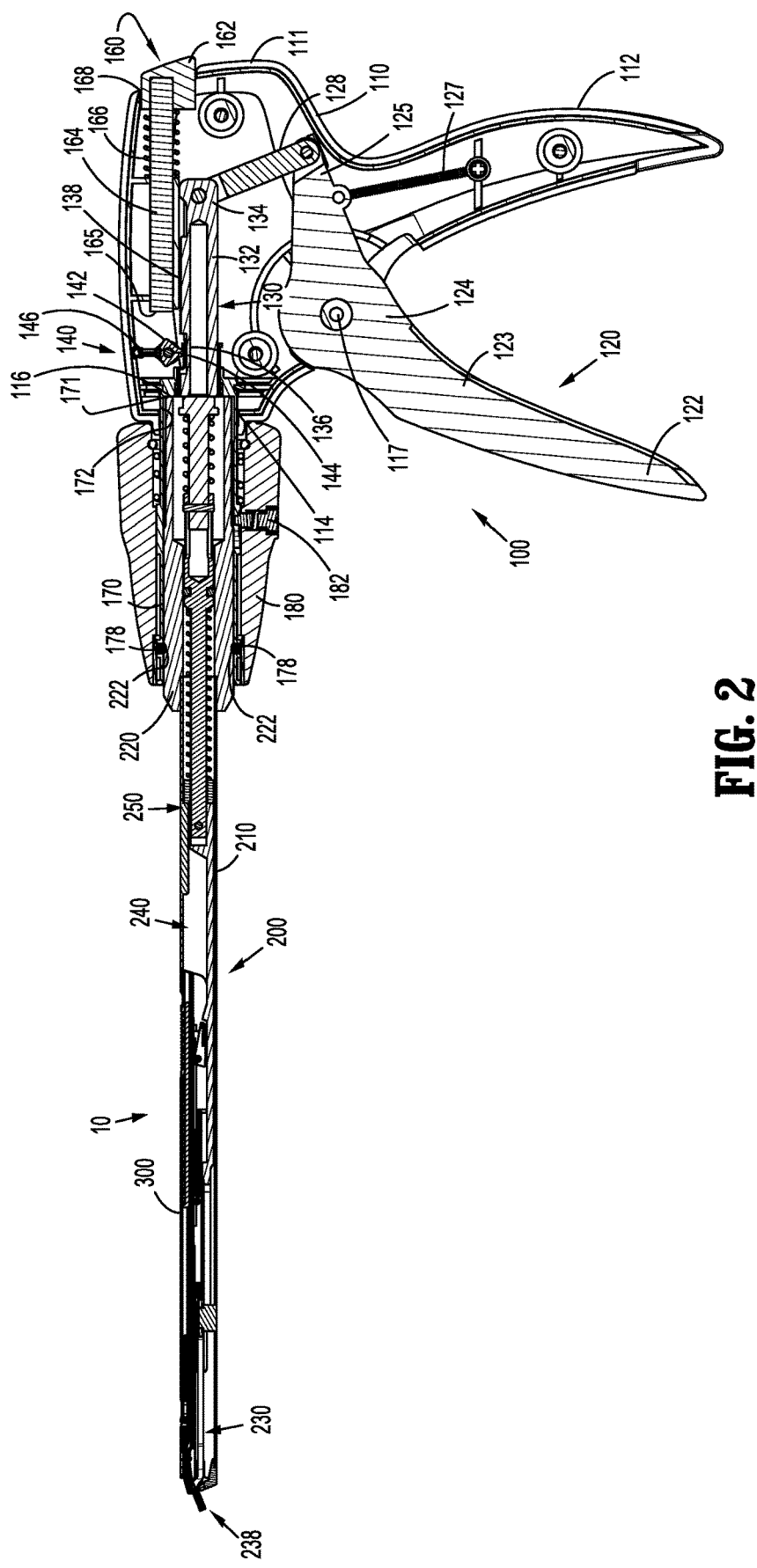
FIG. 2 is a side, longitudinal, cross-sectional view of the clip applier of FIG. 1.
Figure 3:
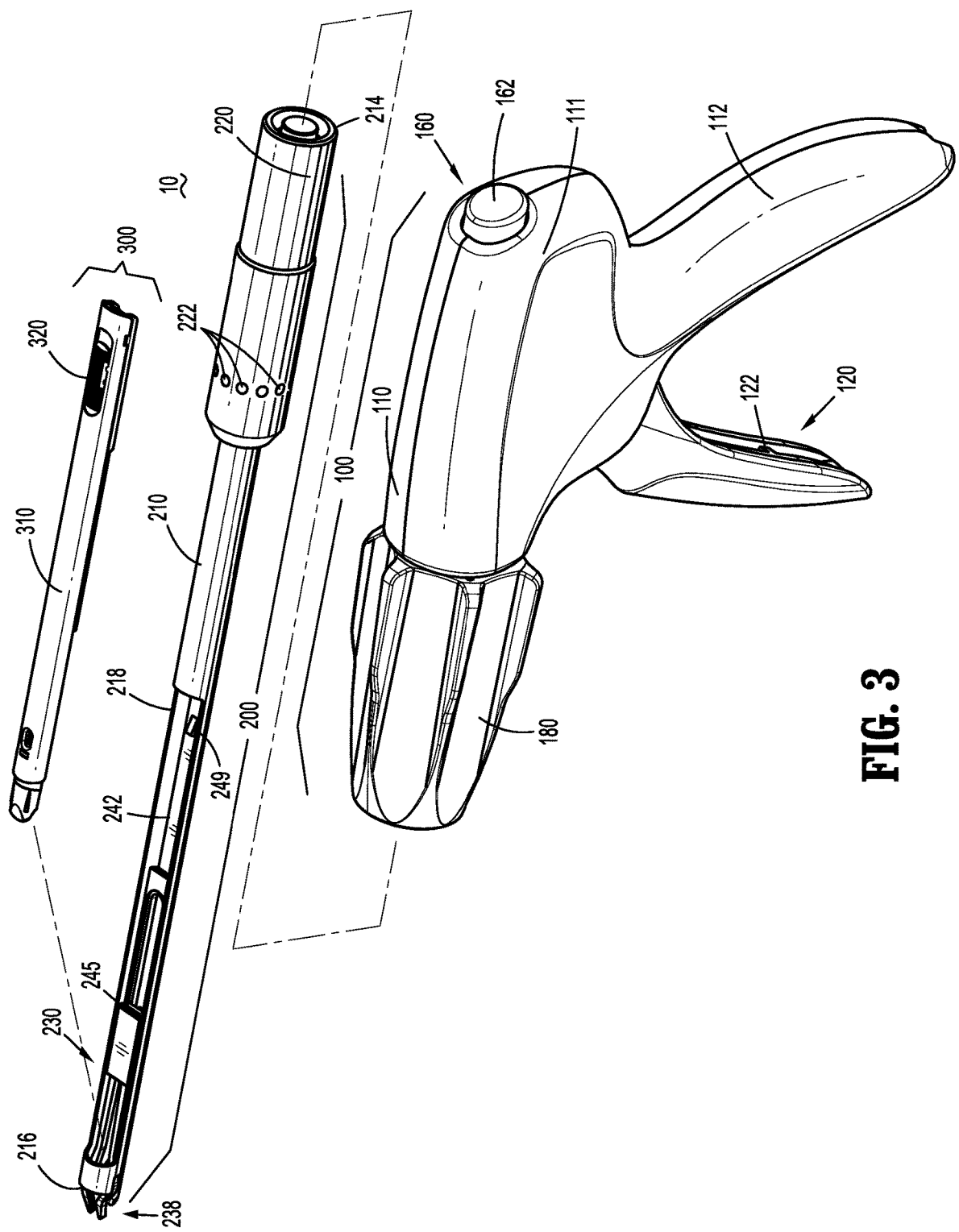
FIG. 3 is a side, perspective view of the clip applier of FIG. 1, disposed in a disassembled condition.

Referring initially to FIGS. 1-3, a reposable multi-fire surgical clip applier provided in accordance with the present disclosure is generally designated as 10. Clip applier 10 includes a handle assembly 100, a shaft assembly 200 extending distally from handle assembly 100, and a clip cartridge assembly 300 mounted within shaft assembly 200. Shaft assembly 200 is removably and selectively engagable with handle assembly 100 and clip cartridge assembly 300 is removably and selectively mountable within shaft assembly 200. Handle assembly 100 and shaft assembly 200 may be configured as sterilizable, reusable components, while clip cartridge assembly 300 may be configured as a single-procedure-use component. As described in detail below, a stack of surgical clips "C" (FIG. 10) is loaded into clip cartridge assembly 300 such that, in operation, each actuation of handle assembly 100 actuates cooperating drive components of handle assembly 100, shaft assembly 200, and cartridge assembly 300 to fire and form a single surgical clip from the stack of surgical clips "C" (FIG. 10) around a vessel or other tissue to ligate the vessel or other tissue.

Figure 4:
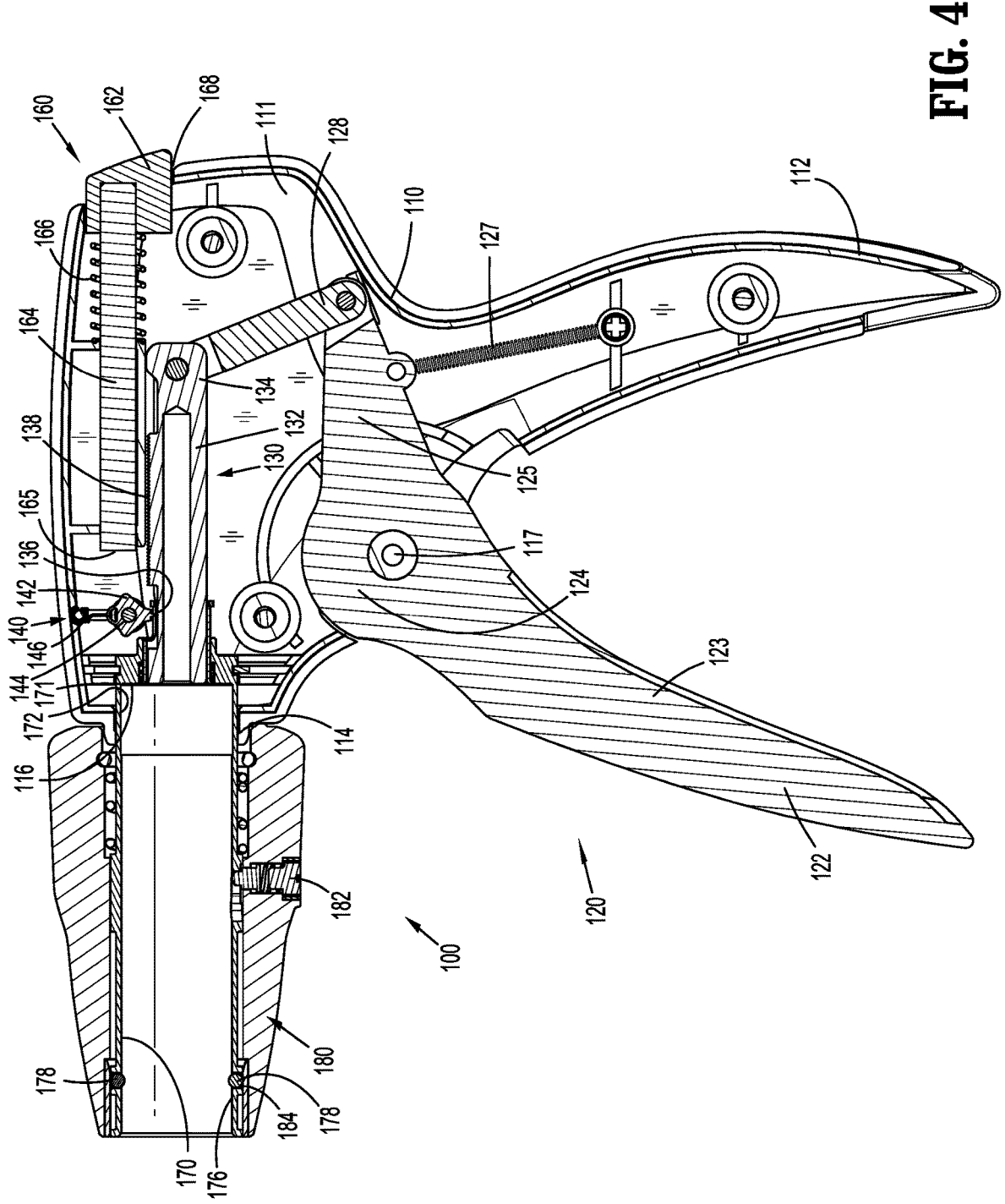
FIG. 4 is a side, longitudinal, cross-sectional view of a handle assembly of the clip applier of FIG. 1.
Figure 5:
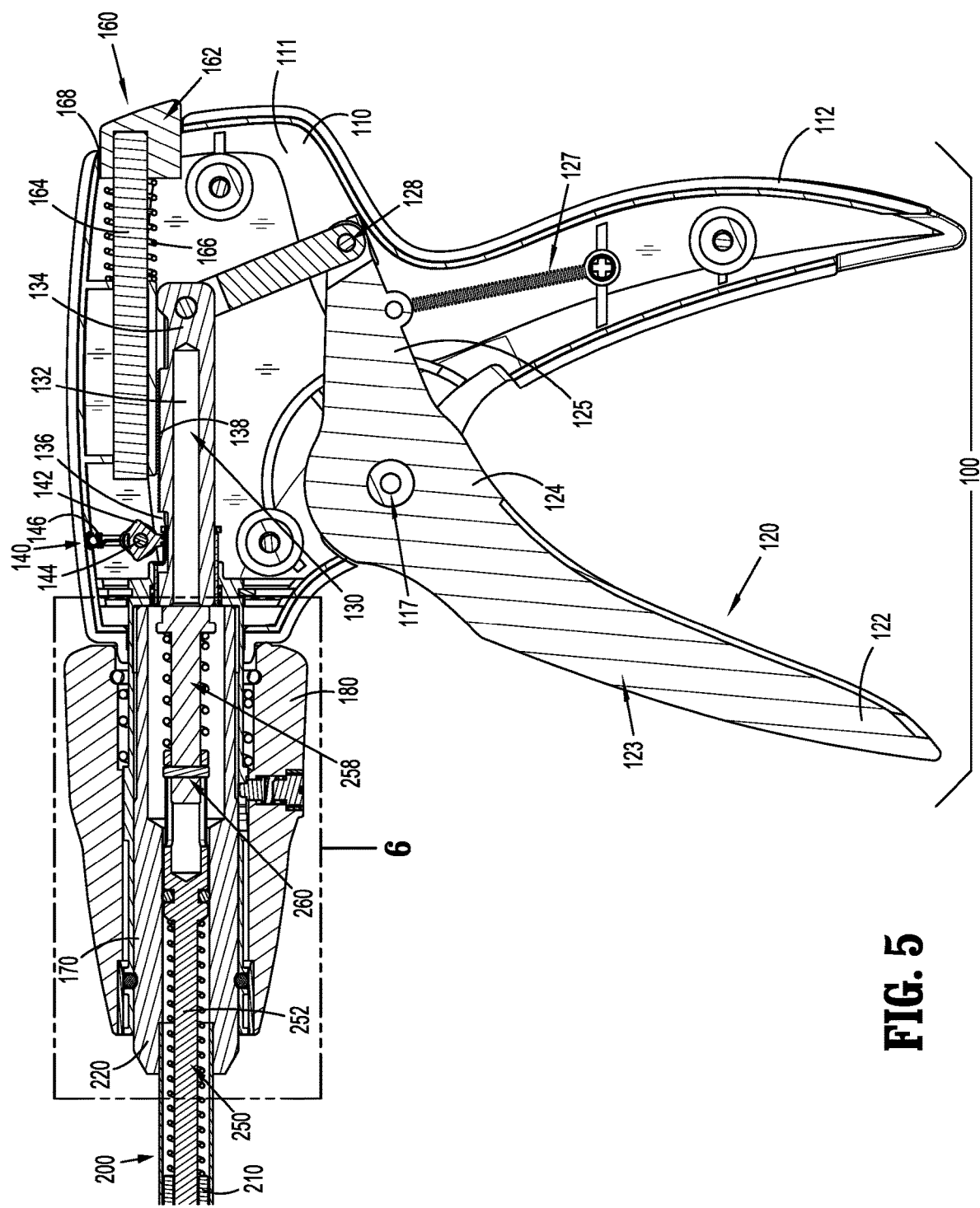
FIG. 5 is a side, longitudinal, cross-sectional view of a proximal portion of the clip applier of FIG. 1, illustrating a shaft assembly engaged with the handle assembly.

With additional reference to FIGS. 4 and 5, handle assembly 100 generally includes a housing 110, a trigger assembly 120 pivotably coupled to housing 110, a drive assembly 130 operably coupled to trigger assembly 120, a ratchet mechanism 140 operably associated with drive assembly 130, a release assembly 160 configured to selectively disengage ratchet mechanism 140, a receiver tube 170 extending distally from housing 110 and configured to receive the proximal hub 220 of shaft assembly 200 upon insertion thereof into handle assembly 100, and a rotation knob 180 disposed about receiver tube 170.

Housing 110 of handle assembly 100 defines a body portion 111 and a fixed handle portion 112 extending downwardly from body portion 111. Housing 110 is configured to house the internal working components of handle assembly 100. Body portion 111 defines an aperture 114 providing access to the interior thereof at a distal end portion of housing 110. A proximal end portion 171 of receiver tube 170 of handle assembly 100 extends through aperture 116 into body portion 111 of housing 110. Proximal end portion 171 of receiver tube 170 defines an annular recess 172 disposed thereabout. A washer 116 mounted within body portion 111 of housing 110 extends into annular recess 172 to rotatably engage receiver tube 170 with housing 110. Rotation knob 180 of handle assembly 100 is engaged about receiver tube 170, e.g., via a set screw 182, in fixed rotational orientation relative thereto such that rotation of rotation knob 180 relative to housing 110 effects similar rotation of receiver tube 170 relative to housing 110.

Body portion 111 of housing 110 further includes a transversely-extending internal pivot post 118 extending between opposing internal surfaces of body portion 111 of housing 110. Fixed handle portion 112 of housing 110 is configured to facilitate grasping of handle assembly 100 and manipulation thereof and is monolithically formed with body portion 111, although other configurations are also contemplated.

Referring to FIGS. 2, 4, and 5, trigger assembly 120 generally includes a trigger 122, a biasing member 127, and a linkage 128. Trigger 122 includes a grasping portion 123, an intermediate pivot portion 124, and a proximal extension portion 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and is configured to receive pivot post 118 of housing 110 so as to enable pivoting of trigger 122 about pivot post 118 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension portion 125 of trigger 122 of trigger assembly 120 is disposed on an opposite side of intermediate pivot portion 124 and, thus, pivot post 118, as compared to grasping portion 123 of trigger 122. As such, pivoting of grasping portion 123 proximally, e.g., towards the actuated position, urges proximal extension portion 125 distally. Proximal extension portion 125 is pivotably coupled to the proximal end of linkage 128. Biasing member 127 is secured at either end and extends between proximal extension portion 125 and fixed handle portion 112 of housing 110. Pivoting of grasping portion 123 towards the actuated position elongates biasing member 127 storing energy therein such that, upon release of grasping portion 123, grasping portion 123 is returned towards the un-actuated position under the bias of biasing member 127. Although illustrated as an extension coil spring, biasing member 127 may define any suitable configuration for biasing grasping portion 123 of trigger 122 towards the un-actuated position.

As noted above, linkage 128 is coupled at its proximal end to proximal extension portion 125 of trigger 122. Linkage 128 is pivotably coupled at its distal end to a proximal extension 134, which extends distally from drive bar 132 of drive assembly 130. As a result of this configuration, pivoting of grasping portion 123 of trigger 122 towards the actuated position urges proximal extension portion 125 of trigger 122 distally which, in turn, urges linkage 128 distally to thereby urge drive bar 132 distally.

Referring still to FIGS. 2, 4, and 5, drive assembly 130 of handle assembly 100 includes drive bar 132, proximal extension 134 of drive bar 132, a distal recess 136 in drive bar 132, and ratchet rack 138. Drive bar 132 extends in a generally longitudinal direction. As noted above, proximal extension 134 extends proximally from drive bar 132 and pivotably couples to linkage 128, thus pivotably coupling drive bar 132 with linkage 128. Ratchet rack 138 extends in a generally longitudinal direction, similar to drive bar 132, and is defined on or engaged with drive bar 132. Distal recess 136 is defined within drive bar 132 and positioned distally of ratchet rack 138.

Ratchet mechanism 140 of handle assembly 100, as noted above, is operably associated with drive assembly 130 to enable ratcheting advancement of drive bar 132. Ratchet mechanism 140 includes a ratchet pawl 142, a pawl pin 144, and a pawl biasing member 146.

Ratchet pawl 142 is pivotably disposed about pawl pin 144, which is mounted transversely within housing 110. Ratchet pawl 142 is disposed in transverse alignment with ratchet rack 138, such that, upon distal advancement of ratchet rack 138, ratchet pawl 142 is incrementally engaged therewith to provide ratcheting functionality. In the un-actuated position of trigger 122, ratchet pawl 142 is disposed within distal recess 136. As a result, ratchet pawl 142 does not engage ratchet rack 138 until an initial portion of the actuation stroke of trigger 122 is completed. Thus, actuation can be aborted prior to completing the initial portion of the actuation stroke, e.g., prior to ratchet pawl 142 engaging ratchet rack 138, with drive assembly 130 returning to the initial condition thereof.

Pawl biasing member 146 of ratchet mechanism 140 is coupled between ratchet pawl 142 and housing 110 so as to bias ratchet pawl 142 towards an operable orientation relative to ratchet rack 138 of drive assembly 130. Pawl biasing member 142 may be configured as a coil extension spring, although other configurations are also contemplated Release mechanism 160 includes a proximal button 162, a distal shaft 164, and a biasing member 166. Proximal button 162 extends through an aperture 168 defined within body portion 111 of housing 110 at a proximal end portion thereof to enable proximal button 162 to be actuated from the exterior of housing 110. Distal shaft 164 is engaged to proximal button 162 and extends distally therefrom within body portion 111 of housing 110. Distal shaft 164 is slidably disposed within body portion 111 of housing 110, transversely aligned with ratchet pawl 142, and defines a distal surface 165. Biasing member 166 is disposed about distal shaft 164 between proximal button 162 and a support disposed within body portion 111 of housing 110 and, although illustrated as a coil spring, may define any suitable configuration. Biasing member 166 is configured to bias proximal button 162 and distal shaft 164 proximally towards an initial position.

Proximal button 162 and distal shaft 164, as noted above, are normally biased towards an initial position. In this initial position, distal surface 165 of distal shaft 164 is proximally spaced-apart from ratchet pawl 142 so as not to interfere with the ratcheting engagement of ratchet pawl 142 with ratchet rack 138 during actuation of trigger assembly 120 and drive assembly 130. Upon depression of proximal button 162 inwardly into housing 110 against the bias of biasing member 166, distal shaft 164 is urged distally though housing 110 such that distal surface 165, in turn, is urged into contact with ratchet pawl 142 to pivot ratchet pawl 142 out of engagement with ratchet rack 138. With ratchet pawl 142 disengaged from ratchet rack 138, trigger assembly 120 and drive assembly 130 are returned towards the un-actuated position under the bias of biasing member 127.

As a result of the above-detailed configuration, release mechanism 160 enables the selective disengagement of ratchet pawl 142 from ratchet rack 138, thus enabling the selective return of trigger assembly 120 and drive assembly 130 towards the un-actuated position at any point during movement of trigger assembly 120 and drive assembly 130 through a full actuation stroke. Thus, handle assembly 100 may be utilized with any suitable shaft assembly 200 and/or clip cartridge assembly 300 to fire surgical clips of various different configurations, e.g., different sizes, shapes, materials, etc., and/or having various different actuation stroke lengths. More specifically, by enabling return of trigger assembly 120 and drive assembly 130 at any point during actuation of trigger assembly 120 and drive assembly 130, clip applier 10 may be reset for subsequent firing after a clip from the stack of surgical clips "C" (FIG. 10) has been fired, even where firing of that clip does not require a full actuation stroke of trigger assembly 120 and drive assembly 130. Notably, ratcheting functionality, as detailed above, is still provided during firing for each of the shaft assemblies 200 and/or clip cartridge assemblies 300 utilized.

With reference to FIGS. 3-6, receiver tube 170 of handle assembly 100, as noted above, defines an annular recess 172 configured to receive washer 118 of housing 110 to rotatably engage receiver tube 170 with housing 110. Rotation knob 180 of handle assembly 100, as also noted above, is engaged about receiver tube 170 via a set screw 182 in fixed rotational orientation relative thereto such that rotation of rotation knob 180 relative to housing 110 effects similar rotation of receiver tube 170 relative to housing 110.

Receiver tube 170 further includes a plurality of apertures 176 defined therethrough and positioned circumferentially thereabout, while rotation knob 180 further defines a plurality of dimples 184 positioned circumferentially about an interior surface thereof in alignment with apertures 176. A plurality of ball bearings 178 is disposed between receiver tube 170 and rotation knob 180 with each ball bearing 178 captured between a dimple 184 of rotation knob 180 and an aperture 176 of receiver tube 170. Apertures 176 define smaller diameters than ball bearings 178 such that a portion of each ball bearing 178 protrudes through the corresponding aperture 176 and such that ball bearings 178 are inhibited from passing entirely through apertures 176. As detailed below, the protruding portions of ball bearings 178, e.g., the portions of ball bearings 178 that protrude inwardly through apertures 176 into the interior of receiver tube 170, are configured for receipt within corresponding dimples 222 defined within proximal collar 220 of shaft assembly 200 to releasably engage shaft assembly 200 with handle assembly 100.

Referring to FIGS. 2, 3, and 5-9, shaft assembly 200 includes an outer tube 210, a proximal collar 220, a jaw assembly 230, and an inner drive assembly 240. Outer tube 210 includes an open distal end portion 212, an open proximal end portion 214, a lumen 216 extending between and communicating with the open distal and proximal end portions, 212, 214, respectively, and an elongated cut-out or window 218 defined through a side wall of outer tube 210 and communicating with lumen 216 therethrough. Elongated cut-out 218 is spaced-apart from open distal end portion 212 of outer tube 210 such that a full circumferential portion of outer tube 210 extends between open distal end 212 and elongated cut-out 218. Elongated cut-out 218 is also spaced-apart from open proximal end portion 214 of outer tube 210 to define a full circumferential portion of outer tube 210 between open proximal end portion 214 and elongated cut-out 218.

Proximal collar 220 is fixedly engaged with and extends proximally from outer tube 210. Proximal collar 220 defines a plurality of dimples 222 positioned circumferentially thereabout. Upon insertion of proximal collar 220 of shaft assembly 200 into receiver tube 170 of handle assembly 100, each ball bearing 178 is configured for receipt within one of the dimples 222 of proximal collar 220 to engage proximal collar 220 of shaft assembly 200 with receiver tube 170 of handle assembly 100 in fixed longitudinal and rotational position relative to receiver tube 170 and rotation knob 180.

Figure 8:
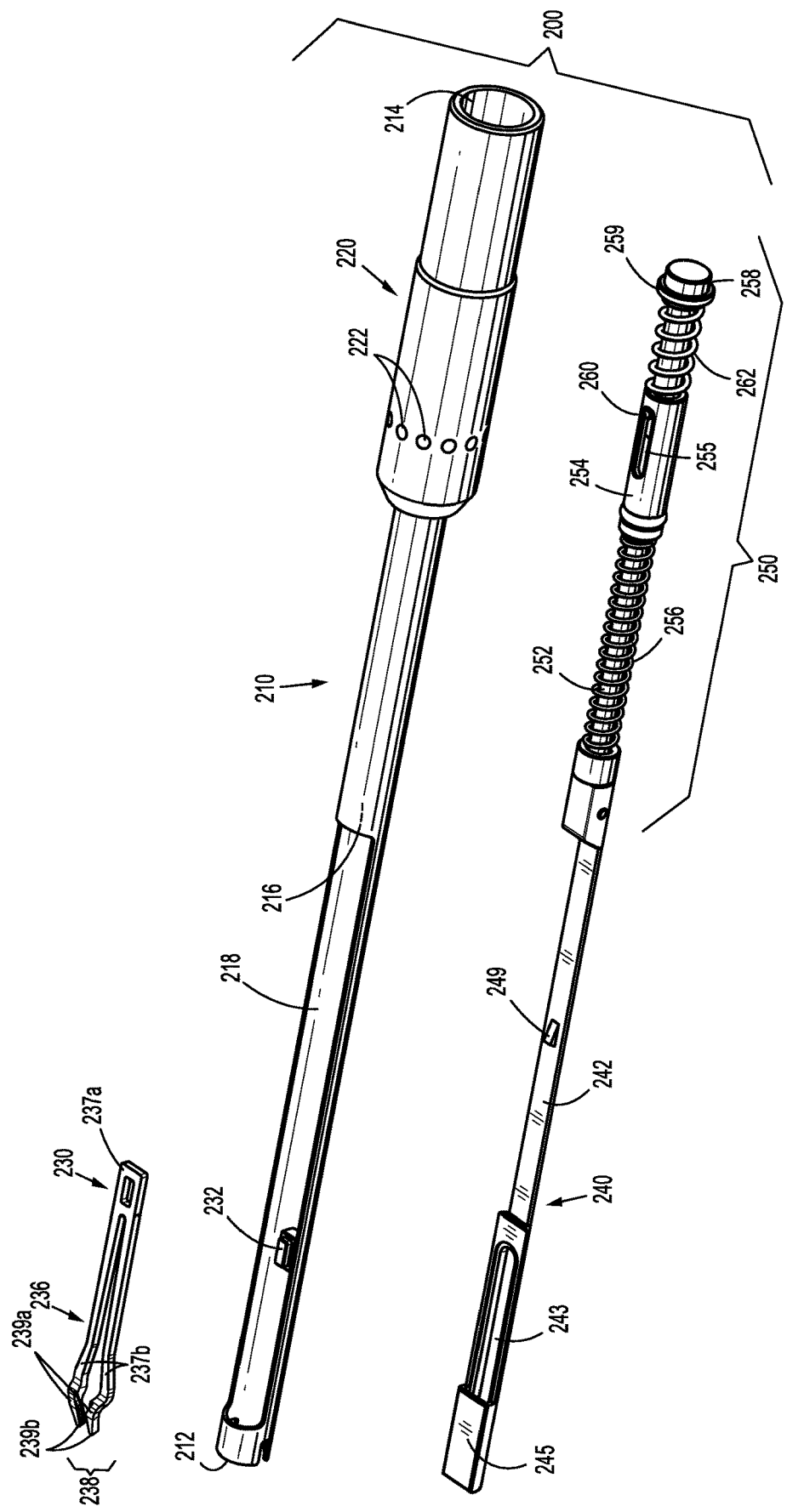
FIG. 8 is an exploded, side, perspective view of the shaft assembly of the clip applier of FIG. 1.
Figure 9:
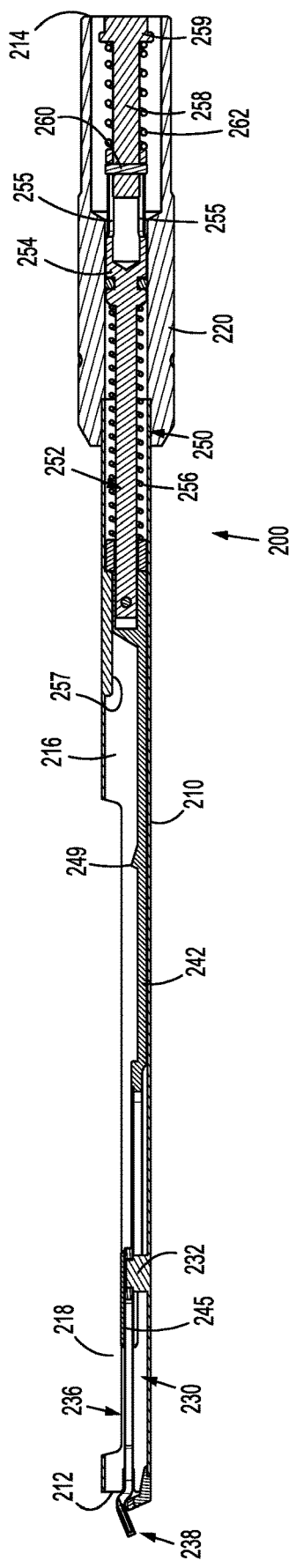
FIG. 9 is a side, longitudinal, cross-sectional view of the shaft assembly of the clip applier of FIG. 1.

With reference to FIGS. 8 and 9, jaw assembly 230 includes a stationary base 232 and a jaws component 236. Stationary base 232 is affixed within outer tube 210 to an interior surface thereof, e.g., via welding. Jaws component 236 includes a proximal hub 237a, a bifurcated neck 237b, and a pair of jaws 238, one of which is attached to the free distal end of each of the bifurcated portions of bifurcated neck 237b. Proximal hub 237a of jaws component 236 is disposed about and engaged to stationary base 232, e.g., via soldering. Bifurcated neck 237b extends distally from proximal hub 237a and distally through outer tube 210 to the pair of jaws 238, which extend distally from open distal end 214 of outer tube 210.

The pair of jaws 238 of jaw assembly 230 is biased apart from one another via bifurcated neck 237b. The pair of jaws 238 defines outwardly-facing cam surfaces 239a and inwardly-facing channels 239b. Boxed distal end portion 245 of distal drive plate 242 of inner drive assembly 240 is configured to engage cam surfaces 239a of the pair of jaws 238 and urge the pair of jaws 238 towards one another, as detailed below. Inwardly-facing channels 239b of the pair of jaws 238 are configured to receive the legs of a surgical clip from the stack of surgical clips "C" (FIG. 10) therein to retain the surgical clip within the pair of jaws 238 during formation thereof, as also detailed below.

Inner drive assembly 240 of shaft assembly 200 includes a distal drive plate 242, and a proximal drive assembly 250. Distal drive plate 242 is disposed within outer tube 210 and defines an elongated slot 243 therethrough and a boxed distal end portion 245 (or other suitable jaws-engaging portion). Elongated slot 243 receives stationary base 232 of jaw assembly 230 to enable distal drive plate 242 to slide through outer tube 210 relative to stationary base 232 and jaws component 236 and to guide such sliding of distal drive plate 242. Boxed distal end portion 245 is configured for positioning about bifurcated neck 237b of jaw assembly 230. Upon distal advancement of distal drive plate 242, boxed distal end portion 245 is advanced distally about jaws component 236 to cam about cam surfaces 239a of the pair of jaws 238 to thereby urge the pair of jaws 238 towards one another. Distal drive plate 242 further includes a wedge 249 disposed thereon and extending upwardly therefrom.

Proximal drive assembly 250 is operably disposed within a proximal portion of outer tube 210 and includes a drive shaft 252 and a plunger 258. Drive shaft 252 is engaged, e.g., pinned, at a distal end portion thereof to a proximal end portion of distal drive plate 242 such that translation of drive shaft 252 of proximal drive assembly 250 through outer tube 210 similarly translates distal drive plate 242 through outer tube 210. Drive shaft 252 includes a proximal hub 254 defining a pair of opposed longitudinally-extending slots 255 (only one of which is illustrated in FIG. 8). A first biasing member 256 is disposed about drive shaft 252 between proximal hub 254 thereof and a stop 257 fixedly disposed within outer tube 210 (see FIG. 9).

Plunger 258 includes an annular protrusion 259 disposed about a proximal end portion thereof and a pin 260 transversely extending through and outwardly from opposed sides of plunger 258 at a distal end portion of plunger 258. The distal end portion of plunger 258, including pin 260, is slidably disposed within proximal hub 254 of drive shaft 252 with the opposed ends of pin 260 extending through the opposed longitudinally-extending slots 255 of proximal hub 254 of drive shaft 252. A second biasing member 262 is disposed about plunger 258 between annular protrusion 259 and the proximal end of proximal hub 254 of drive shaft 252.

With additional reference to FIG. 5, a proximally-facing surface of plunger 258 is configured to abut drive bar 132 of drive assembly 130 of handle assembly 100 upon engagement of shaft assembly 200 with handle assembly 100. In this manner, as drive bar 132 is advanced distally, drive bar 132 urges plunger 258 to likewise translate distally, as detailed below.

First and second biasing members 256, 262, respectively, enable, in response to actuation of trigger 122 (FIGS. 1-3), appropriate translation of distal drive plate 242 through outer tube 210 and relative to jaw assembly 230 to advance boxed distal end portion 245 of distal drive plate 242 about cam surfaces 239a of the pair of jaws 238, thereby urging the pair of jaws 238 towards one another to form a surgical clip from the stack of surgical clips "C" (FIG. 10) about a vessel disposed between the pair of jaws 238. First biasing member 256 has a first spring constant which is less than a second spring constant of second biasing member 262.

As a result of the above-detailed configuration, as trigger 122 is pivoted towards the actuated position, drive bar 132 is advanced distally, eventually contacting plunger 258. Due to first spring constant of first biasing member 256 being less than second spring constant of second biasing member 262, as drive bar 132 is initially urged into plunger 258, plunger 258 and drive shaft 252 translate together distally such that first biasing member 256 is compressed while second biasing member 262 remains substantially un-compressed.

As drive shaft 252 is translated distally, the pair of jaws 238 is urged towards one another to form a surgical clip from the stack of surgical clips "C" (FIG. 10) about a vessel disposed between the pair of jaws 238. As can be appreciated, depending upon the specific shaft assembly 200 used, manufacturing tolerances, the configuration of the clip "C" (FIG. 10) being formed, and/or other factors, the required travel distance of drive shaft 252 to fully form the surgical clip "C" (FIG. 13) may vary.

Once the pair of jaws 238 have been fully approximated against one another or fully closed on the surgical clip, and/or when the opposed ends of pin have reached the distal ends of longitudinally-extending slots 255b of proximal hub 254, drive shaft 252 is no longer permitted to travel further distally. Thus, upon further distal urging of drive bar 132, e.g., to complete the actuation stroke of trigger 122, plunger 258 is advanced distally independently of drive shaft 252 to compress second biasing member 262. Thus, the compression of second biasing member 262 enables drive shaft 252 (and, thus, distal drive plate 242) to remain in position despite further actuation of trigger 122. This configuration serves as a safety feature, whereby compression of second biasing member 262 inhibits over-loading of distal drive plate 242 and potential damage resulting from forced advancement of distal drive plate 242 in the instance of a jam, other malfunction, too large or too tough of a structure disposed between the pair of jaws 238, etc. This configuration also enables use of shaft assembly 200 with various different handle assemblies 100 having different actuation stroke lengths.

Referring to FIGS. 1, 3, and 10-12, clip cartridge assembly 300 includes a cartridge cover 310, a locking slider 320, a clip carrier 330, a clip follower 340, a clip pusher 350, a biasing member 360, a pivoting wedge assembly 370, and a stack of surgical clips "C." Cartridge cover 310 includes an arcuate top surface 312 and a pair of spaced-apart side walls 314 depending from arcuate top surface 312 and cooperating therewith to define an internal cavity 316. With clip cartridge assembly 300 mounted within shaft assembly 200, arcuate top surface 312 is disposed within elongated cut-out 218 of outer tube 210, substantially flush with the outer surface of outer tube 210. Side walls 314 may include engagement features (not shown) disposed along the length thereof and configured to retain clip carrier 330 in engagement with cartridge cover 310, thereby enclosing internal cavity 316. Arcuate top surface 312 of cartridge cover 310 further defines a window 318 therethrough towards a proximal end portion of cartridge cover 310. Window 318 communicates with internal cavity 316.

Locking slider 320 is disposed within internal cavity 316 of cartridge cover 310. Locking slider 320 includes a base 322 supporting a cap 324 thereon and defining a proximal extension 325 and a distal extension 326. "Unlocked" indicia, e.g., a symbol of an open lock in a first color, may be provided proximal extension 325 and/or "locked" indicia, e.g., a symbol of a closed lock in a second, different color, may be provided on distal extension 326. Locking slider 320 is retained in slidable engagement with cartridge cover 310 via an engagement clip 328.

Cap 324 of locking slider 320 is configured for slidable receipt within window 318 of cartridge cover 310 and is accessible through window 318 to enable manual sliding of locking slider 320 between a distal, unlocked position and a proximal, locked position. In the distal, unlocked position, proximal extension 325 does not extend proximally beyond the proximal end portion of cartridge cover 310. In the proximal, locked position, proximal extension 325 extends proximally beyond the proximal end portion of cartridge cover 310. As detailed below, movement of locking slider 330 between the distal and proximal positions enables selective locking and unlocking of clip cartridge assembly 300 from within shaft assembly 200.

With continued reference to FIGS. 1, 3, and 10-12, clip carrier 330 of clip cartridge assembly 300 includes a floor 332, a hook 334 depending from floor 332, and a pair of ramped arms 336 extending distally from floor 332 in an inclined-orientation relative thereto. Clip carrier 330 is configured for positioning within internal cavity 316 of cartridge cover 310 and may include complementary engagement features (not shown) disposed along the length thereof that are configured to engage the engagement features (not shown) of side walls 314 to engage clip carrier 330 with and in fixed position relative to cartridge cover 310.

Clip carrier 330 further includes a resilient central tang 338 coupled thereto and extending from floor 332 between arms 336. Resilient central tang 338 is configured to engage a backspan of a distal-most surgical clip of the stack of surgical clips "C" to retain the stack of surgical clips "C" within clip carrier 330 prior to actuation.

Clip follower 340 of clip cartridge assembly 300 includes a distal sled 342 slidably disposed within clip carrier 330 proximally of the stack of surgical clips "C." Distal sled 342 of clip follower 340, more specifically, is configured for positioning proximally adjacent the proximal-most clip of the stack of surgical clips "C" in abutting relation therewith. Clip follower 340 further includes an elongated rod 344 extending proximally from distal sled 342. Elongated rod 344 defines a fixed distal end engaged to distal sled 342 and a free proximal end that is slidably disposed within a lumen defined within base 322 of locking slider 320. A biasing member 346 is disposed about elongated rod 344 of clip follower 340 between distal sled 342 and base 322 of locking slider 320 so as to bias distal sled 342 distally into the proximal-most clip of the stack of surgical clips "C," thereby biasing the stack of surgical clips "C" distally such that, as the distal-most clip is loaded into the pair of jaws 238 (FIGS. 8-9), the remaining clips in the stack of surgical clips "C" are urged distally to replace the previously-loaded clip.

With continued reference to FIGS. 1, 3, and 10-12, clip pusher 350 of clip cartridge assembly 300 is slidably disposed about an underside of clip carrier 330 (e.g., opposite clip follower 340). Clip pusher 350 includes a pair of pusher flanges 352 at a distal end portion thereof that is configured to urge a distal-most surgical clip of the stack of surgical clips "C" distally over resilient central tang 338 of clip carrier 330 and distally from clip cartridge assembly 300 into the pair of jaws 238 (FIGS. 8 and 9). Clip pusher 350 further includes a wedge base 354 defining a pair of spaced-apart walls disposed towards the proximal end portion thereof.

Figure 10:
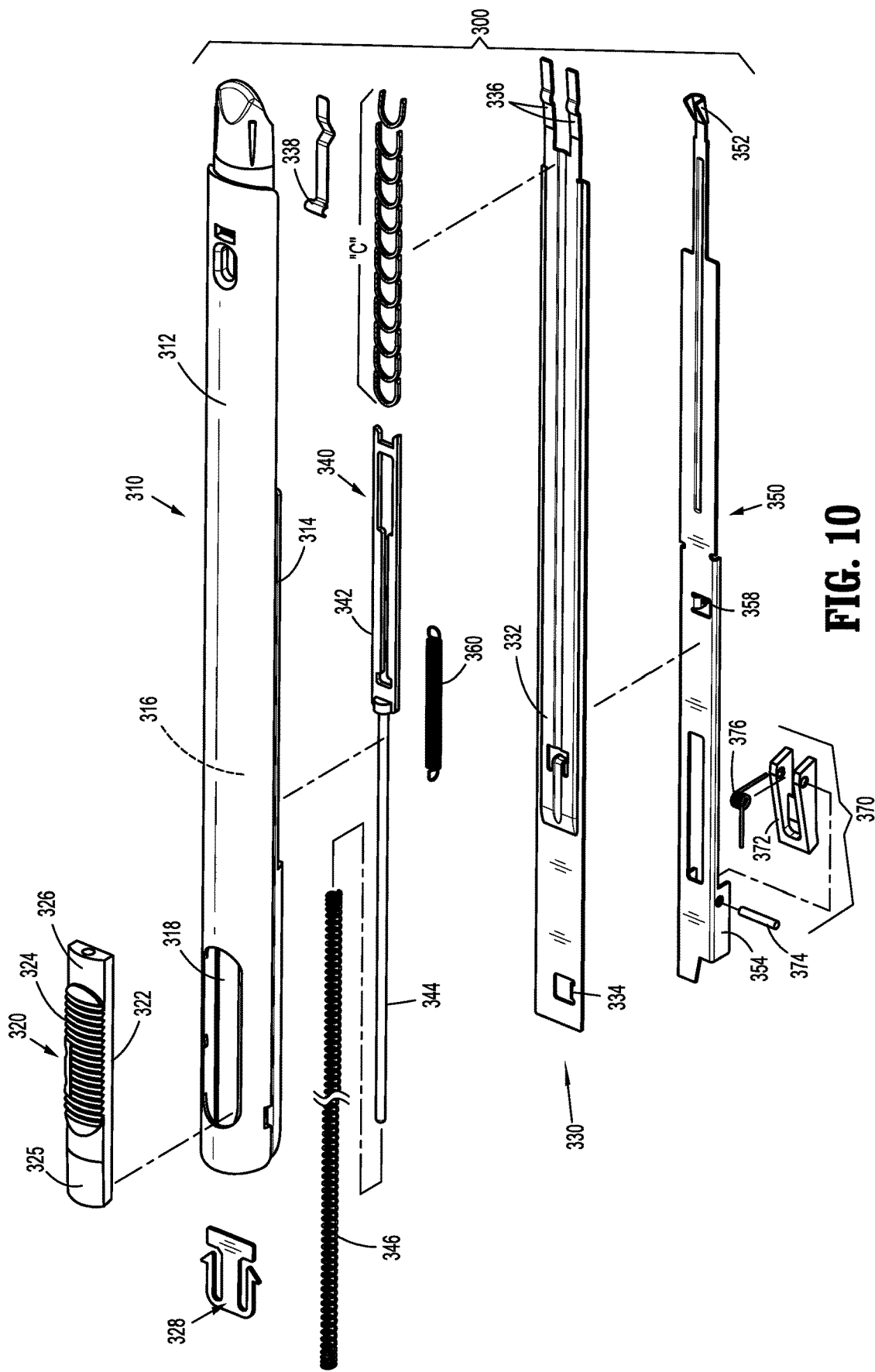
FIG. 10 is an exploded, side, perspective view of a clip cartridge assembly of the clip applier of FIG. 1.
Figure 11A:
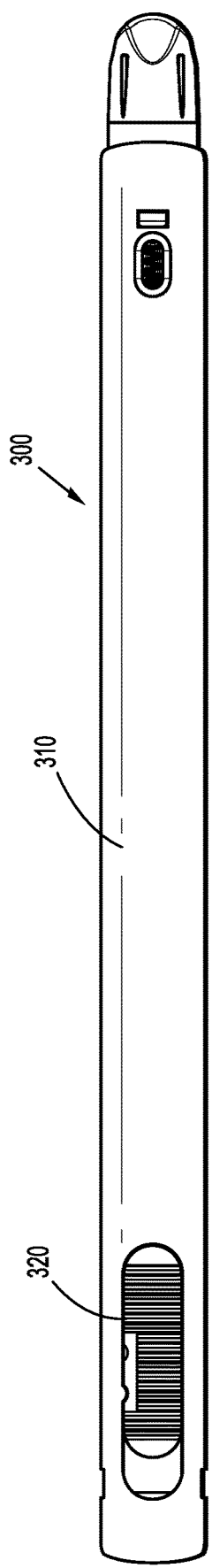
FIG. 11A is a top view of the clip cartridge assembly of the clip applier of FIG. 1.
Figure 11B:
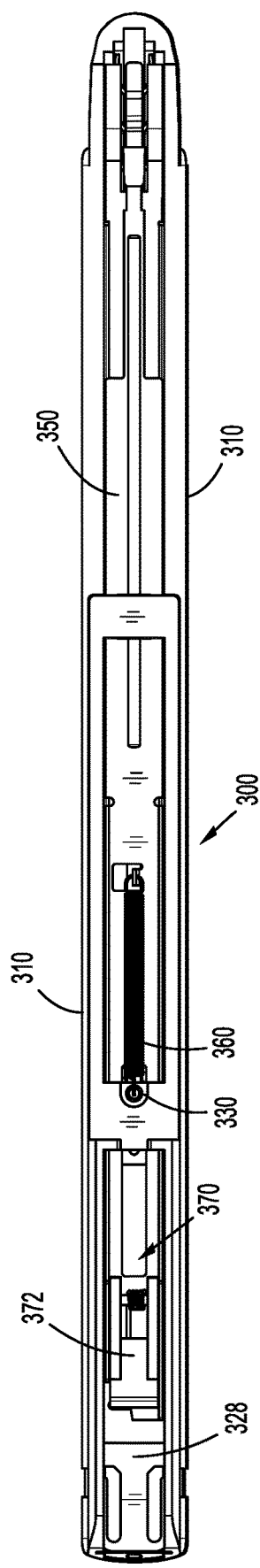
FIG. 11B is a bottom view of the clip cartridge assembly of the clip applier of FIG. 1.
Figure 11C:
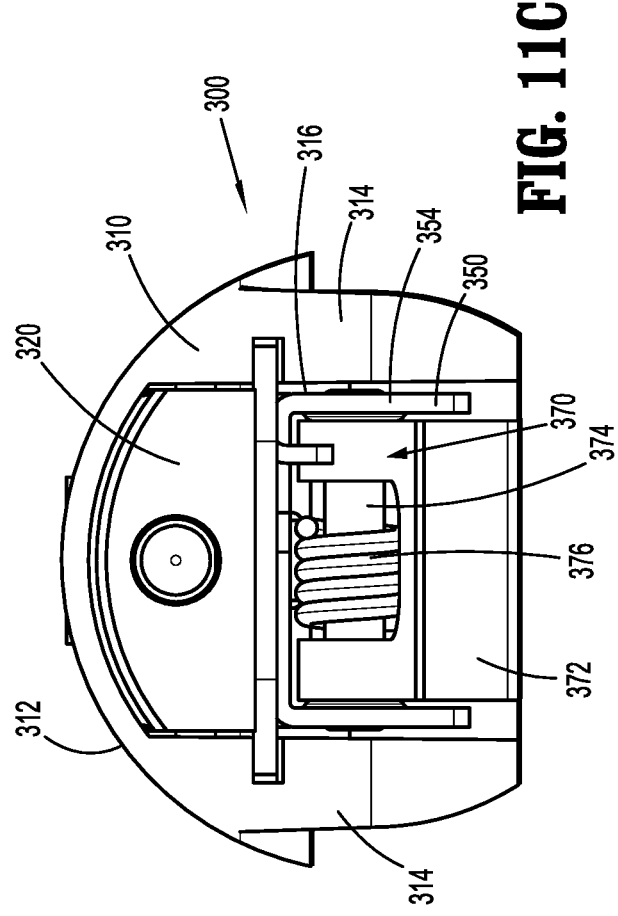
FIG. 11C is a transverse, cross-sectional view of the clip cartridge assembly of the clip applier of FIG. 1.
Figure 12:
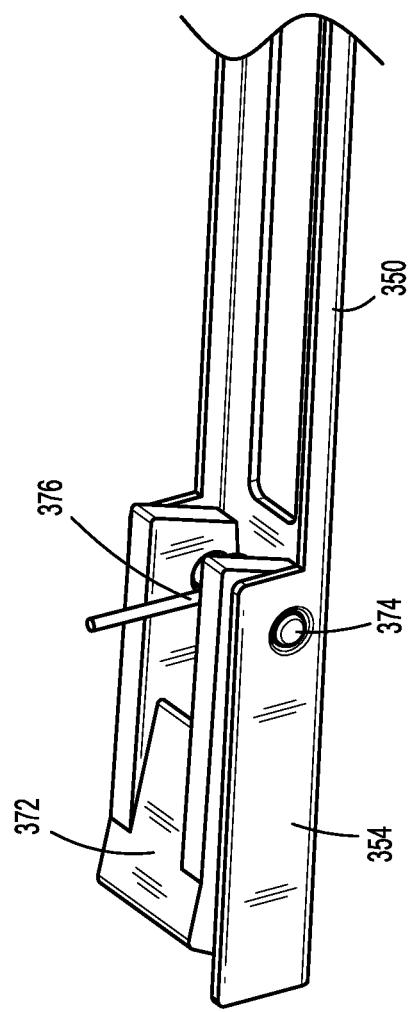
FIG. 12 is a side, perspective view of a proximal end portion of a clip pusher of the clip cartridge assembly of the clip applier of FIG. 1, disposed in an inverted orientation.

With reference to FIGS. 10, 11C, and 12, pivoting wedge assembly 370 is operably coupled to wedge base 354 of clip pusher 350 and includes a wedge pusher 372 pivotably coupled to between the spaced-apart walls of wedge base 354 of clip pusher 350 via a pivot pin 374. Pivoting wedge assembly 370 further includes a torsion spring 376 disposed about pivot pin 374 so as to bias wedge pusher 372 towards a position wherein the proximal end portion thereof protrudes from wedge base 354 of clip pusher 350.

Referring again to FIGS. 1, 3, and 10-12, upon insertion of clip cartridge assembly 300 into outer tube 210, wedge 249 of distal drive plate 242 is positioned proximally adjacent wedge pusher 372 of pivoting wedge assembly 370 of clip pusher 350. In this manner, as detailed below, upon distal advancement of distal drive plate 242, wedge 249 is urged into wedge pusher 372 to similarly advance clip pusher 350 distally.

Clip pusher 350 further includes a ring 358 depending therefrom. Ring 358 is configured to receive a distal end portion of biasing member 360 to fix the distal end portion of biasing member 360 relative to clip pusher 350. The proximal end portion of biasing member 360 is configured for receipt by hook 334 of clip carrier 330 to fix the proximal end portion of biasing member 360 relative to clip carrier 330. Biasing member 360 acts as an extension spring to bias clip pusher 350 towards a more-proximal position and to return clip pusher 350 towards the more-proximal position after distal advancement thereof to load a distal-most surgical clip of the stack of surgical clips "C" into the pair of jaws 238 (FIGS. 8-9).

Referring generally to FIGS. 1-12, in order to engage shaft assembly 200 with handle assembly 100 in preparation for use, proximal hub 220 of shaft assembly 200 is inserted into rotation knob 180 and receiver shaft 170 of handle assembly 100 such that ball bearings 178 are engaged within dimples 222 of proximal hub 220 of shaft assembly 100. In this engaged position, drive bar 132 is operably positioned proximally adjacent inner drive assembly 240 of shaft assembly 200. Disengagement and removal of shaft assembly 200 is effected in the opposite manner as the insertion and engagement detailed above.

To engage clip cartridge assembly 300 within shaft assembly 200, locking slider 320 of clip cartridge assembly 300, if not already in the unlocked, distal position, is moved to the unlocked, distal position. With locking slider 320 in the unlocked, distal position, clip cartridge assembly 300 is inserted through elongated cut-out 218 of outer tube 210 of shaft assembly 200 and distally relative to outer tube 210 such that the distal end portion of cartridge cover 310 ducks under outer tube 210 distally of cut-out 218. Following the positioning of the distal end portion of cartridge cover 310 in this manner, the remainder of clip cartridge assembly 300 is inserted through elongated cut-out 218 to be seated within outer tube 210. As clip cartridge assembly 300 is seated within outer tube 210, wedge 249 of inner drive assembly 240 of shaft assembly 200 is positioned proximally adjacent wedge pusher 372 of wedge assembly 370 of clip cartridge assembly 300.

Once clip cartridge assembly 300 is fully seated within lumen 216 of outer tube 210 with the distal end portion of cartridge cover 310 extending through tubular distal segment 219a of outer tube 210, locking slider 320 is moved from the distal, unlocked positioned to the proximal locked position such that proximal extension 325 of locking slider 320 is extended proximally beyond the proximal end portion of cartridge cover 310 and into outer tube 210, proximally of cut-out 218. Thus, with proximal extension 325 of locking slider 320 extending proximally of cut-out 218 if outer tube 210 the distal end portion of cartridge cover 310 extending distally of cut-out 218 through outer tube 210, clip cartridge assembly 300 is locked in engagement within shaft assembly 200. Disengagement and removal of clip cartridge assembly 300 is effected in the opposite manner as the insertion and engagement detailed above.

Continuing with general reference to FIGS. 1-12, in use, clip applier 10 is manipulated into position such that a vessel to be ligated is disposed between the pair of jaws 238 of jaw assembly 230. Thereafter, grasping portion 123 of trigger 122 is pivoted towards fixed handle portion 112 of housing 110 to urge linkage 128 distally which, in turn, urges drive bar 132 distally through housing 110 and proximal hub 220 and into contact with the proximally-facing surface of plunger 258 such that plunger 258 is likewise translated distally.

As drive bar 132 is initially urged into plunger 258, plunger 258 and drive shaft 252 translate together distally such that first biasing member 256 is compressed while second biasing member 262 remains substantially un-compressed. This distal translation of drive shaft 252 urges similar distal translation of distal drive plate 242, which, as a result of the positioning of wedge 249 of distal drive plate 242 proximally adjacent wedge pusher 372 of wedge assembly 370, urges wedge 249 into wedge pusher 372 to advance clip pusher 350 distally to thereby urge a distal-most surgical clip of the stack of surgical clips "C" distally over resilient central tang 338 of clip carrier 330 and distally from clip cartridge assembly 300 into the pair of jaws 238. Slightly delayed from the loading of the distal-most clip into the pair of jaws 238, the distal translation of distal drive plate 242 also urges boxed distal end portion 245 of distal drive plate 242 about cam surfaces 239a of the pair of jaws 238, thereby urge the pair of jaws 238 towards one another to form the previously-loaded surgical clip about the vessel disposed between the pair of jaws 238.

As drive bar 132 is translated distally to effect the above, ratchet pawl 142 incrementally engages ratchet rack 138, inhibiting proximal return of drive bar 132. Trigger 122 is thus likewise inhibited from returning towards the un-actuated position. Drive bar 132 and trigger 122 are permitted to return towards the un-actuated position upon actuation of release mechanism 160, as detailed above, or after a full actuation of trigger 122 has been completed and ratchet pawl 142 has cleared ratchet rack 138. In this manner, the above-detailed firing may be accomplished in a continuous stroke or incrementally and may be reset at any point during firing.

Once the pair of jaws 238 have been fully approximated against one another, fully closed on the surgical clip and/or about tissue, or in the event of an over-load condition, rather than further actuation of trigger 122 urging drive shaft 252 further distally, second biasing member 262 is compressed such that plunger 258 is advanced distally independently of drive shaft 252. Thus, the compression of second biasing member 262 enables drive shaft 252 (and, thus, distal drive plate 242) to remain in position while the full actuation stroke of trigger 122 is completed. This configuration also permits the full actuation stroke of trigger 122 to be completed and serves as an over-load protection safety feature, as detailed above.

Upon actuation of release mechanism 160 or full actuation of trigger 122, e.g., upon reaching the actuated position of trigger 122, ratchet pawl 142 is disengaged from ratchet rack 138, thus permitting trigger 122 to be returned to the un-actuated position under the bias of biasing member 127. As such, drive bar 132, plunger 248, drive shaft 252, distal drive plate 242, and clip pusher 350 are returned proximally under their respective biases. The above may then be repeated to form additional surgical clips about vessels to ligate the vessels.

The present disclosure contemplates that clip applier 10 be capable of loading different surgical clip cartridge assemblies 300 within shaft assembly 200. Specifically, surgical clip applier 10 may be loaded with a clip cartridge assembly 300 having a stack of surgical clips "C" of a particular size and/or configuration. For example, depending upon a particular purpose, a first clip cartridge assembly 300 having a stack of surgical clips "C" of a first size or a second clip cartridge assembly 300 having a stack of surgical clips "C" of a second size different than the first size may be loaded into shaft assembly 200. Additionally, during a surgical procedure, if the need arises to use a different size and/or configuration of surgical clip, the user may remove the clip cartridge assembly 300 being used in favor of a different clip cartridge assembly 300.

The present disclosure further contemplates a surgical kit including one handle assembly 100, one shaft assembly 200, and one or more clip cartridge assemblies 300 (similar or different from one another). The kit may also include instructions for the assembly of clip applier 10, the use of clip applier 10, and/or the reprocessing of reusable components of clip applier 10 following use. A package, container, or box may also be provided.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
   a handle assembly, including:
     a housing;
     a trigger movable relative to the housing;
     a drive bar disposed within the housing and operably coupled to the trigger such that actuation of the trigger moves the drive bar distally through the housing, the drive bar including a ratchet rack;
     a ratchet pawl disposed within the housing, wherein, in an operable position of the ratchet pawl, the ratchet pawl is configured to incrementally engage the ratchet rack upon distal movement of the drive bar; and
     a release mechanism operably coupled to the housing, the release mechanism including a release button and a shaft extending from the release button, the release button selectively actuatable to urge the shaft, in a first direction, into the ratchet pawl, thereby moving the ratchet pawl from the operable position to a disengaged position, wherein the ratchet pawl is disengaged from the ratchet rack, wherein, upon a movement of the shaft in a second direction, opposite the first direction, the ratchet pawl automatically moves from the disengaged position to the operable position;
   a shaft assembly releasably engagable with the handle assembly, the shaft assembly including an outer tube, a pair of jaws supported at a distal end portion of the outer tube, and a drive assembly slidably disposed within the outer tube; and
   a clip cartridge assembly releasably engagable within the shaft assembly, the clip cartridge assembly including a stack of surgical clips operably supported therein;
   wherein, when the shaft assembly is releasably engaged with the handle assembly and the clip cartridge assembly is releasably engaged within the shaft assembly, actuation of the trigger moves the drive assembly distally to load a distal-most clip of the stack of surgical clips into the pair of jaws, and to cam the pair of jaws towards one another to form the distal-most clip about tissue.

2. The reposable surgical clip applier according to claim 1, further comprising a pawl biasing member configured to bias the ratchet pawl towards the operable position.

3. The reposable surgical clip applier according to claim 1, wherein the ratchet pawl is pivotably coupled to the housing about a pawl pin, and wherein the shaft of the release mechanism is configured to urge the ratchet pawl to pivot about the pawl pin from the operable position to the disengaged position.

4. The reposable surgical clip applier according to claim 1, further comprising a biasing member configured to bias the drive bar proximally relative to the housing such that, upon disengagement of the ratchet pawl from the ratchet rack, the drive bar is returned proximally under the bias of the biasing member.

5. The reposable surgical clip applier according to claim 1, wherein the release button is movable between an un-actuated position, wherein the release button extends proximally from the housing, and an actuated position, wherein the release button is depressed at least partially into the housing.

6. The reposable surgical clip applier according to claim 5, further comprising a biasing member configured to bias the release button towards the un-actuated position.

7. The reposable surgical clip applier according to claim 1, wherein the outer tube of the shaft assembly defines an elongated cut-out, and wherein the clip cartridge assembly is removably insertable into the elongated cut-out to releasably engage the clip cartridge assembly within the shaft assembly.

8. The reposable surgical clip applier according to claim 7, wherein the clip cartridge assembly includes a locking slider movable between an unlocked position and a locked position to releasably lock the clip cartridge assembly within the outer tube.

9. The reposable surgical clip applier according to claim 1, wherein the handle assembly further includes a receiver tube extending distally from the housing, the receiver tube defining an interior and including a plurality of ball bearings arranged circumferentially thereabout and extending partially into the interior, and wherein the shaft assembly includes a proximal collar defining a plurality of dimples arranged circumferentially thereabout, the dimples configured to receive the ball bearings upon insertion of the proximal collar into the receiver tube to engage the shaft assembly with the handle assembly.

10. The reposable surgical clip applier according to claim 9, further comprising a rotation knob disposed about and engaged with the receiver tube, wherein, with the shaft assembly engaged with the handle assembly, rotation of the rotation knob relative to the housing similarly rotates the shaft assembly relative to the housing.

11. A reposable surgical clip applier, comprising:
a handle assembly including a trigger and a drive bar operably coupled to the trigger such that actuation of the trigger moves the drive bar distally;
a shaft assembly releasably engagable with the handle assembly, the shaft assembly including an outer tube, a pair of jaws supported at a distal end portion of the outer tube, and a drive assembly slidably disposed within the outer tube, the drive assembly including:
a jaws-engaging portion and a first wedge; and
a proximal drive assembly and a distal drive plate extending distally from the proximal drive assembly, the first wedge disposed on the distal drive plate of the drive assembly, wherein the proximal drive assembly includes:
a plunger;
a drive shaft coupled to and extending distally from the plunger;
a first biasing member configured to bias the drive shaft proximally relative to the outer tube; and
a second biasing member configured to bias the plunger proximally relative to the drive shaft; and
a clip cartridge assembly releasably engagable within the shaft assembly, the clip cartridge assembly including a clip carrier, a stack of surgical clips supported on the clip carrier, and a clip pusher slidable relative to the clip carrier, the clip pusher including a second wedge pivotably coupled thereto towards a proximal end portion thereof;
wherein, when the shaft assembly is releasably engaged with the handle assembly and the clip cartridge assembly is releasably engaged within the shaft assembly, the first wedge is operably positioned relative to the second wedge and the drive bar is operably positioned relative to the drive assembly such that actuation of the trigger moves the drive assembly distally to move the clip pusher distally to load a distal-most clip of the stack of surgical clips into the pair of jaws, and to move the jaws-engaging portion distally to cam the pair of jaws towards one another to form the distal-most clip about tissue.

12. The reposable surgical clip applier according to claim 11, wherein the clip pusher includes a wedge base disposed at a proximal end portion thereof, the wedge base including pair of spaced-apart walls, wherein a pivot pin extends between the spaced-apart walls to pivotably couple the second wedge to the wedge base towards a proximal end portion thereof.

13. The reposable surgical clip applier according to claim 12, further comprising a torsion spring disposed about the pivot pin and configured to bias the second wedge to extend from the wedge base.

14. The reposable surgical clip applier according to claim 11, wherein the distal drive plate defines the jaws-engaging portion at a distal end portion thereof.

15. The reposable surgical clip applier according to claim 11, wherein the first biasing member defines a spring constant that is less than a spring constant of the second biasing member such that, upon initial distal urging of the plunger, the first spring compresses to enable the plunger and the drive shaft to move together distally through the outer tube, and wherein, upon further distal urging of the plunger, the second spring compresses such that the plunger moves distally through the outer tube independently of the drive shaft.

16. The reposable surgical clip applier according to claim 11, wherein the outer tube of the shaft assembly defines an elongated cut-out, and wherein the clip cartridge assembly is removably insertable into the elongated cut-out to releasably engage the clip cartridge assembly within the shaft assembly.

17. The reposable surgical clip applier according to claim 16, wherein the clip cartridge assembly includes a locking slider movable between an unlocked position and a locked position to releasably lock the clip cartridge assembly within the outer tube.

18. The reposable surgical clip applier according to claim 11, wherein the drive bar of the handle assembly includes a ratchet rack disposed thereon, and wherein the handle assembly further includes a ratchet pawl configured to incrementally engage the ratchet rack upon distal advancement of the drive bar.

* * * * *